United States Patent [19]

Walz et al.

[11] 4,456,554
[45] Jun. 26, 1984

[54] AMMONIUM COMPOUNDS

[75] Inventors: Klaus Walz; Karl Schäfer; Günther Hoffarth, all of Leverkusen; Hans Schulze, Cologne, all of Fed. Rep. of Germany

[73] Assignee: Bayer Aktiengesellschaft, Leverkusen, Fed. Rep. of Germany

[21] Appl. No.: 417,828

[22] Filed: Sep. 13, 1982

[30] Foreign Application Priority Data

Sep. 17, 1981 [DE] Fed. Rep. of Germany ....... 3137043

[51] Int. Cl.$^3$ .............................................. C11C 3/00
[52] U.S. Cl. .................................................. 260/403
[58] Field of Search ........................................ 260/403

[56] References Cited

U.S. PATENT DOCUMENTS

| Re. 30,748 | 9/1981 | Sears ................... 260/403 |
| 3,539,601 | 10/1970 | Lewis ................... 260/403 |
| 4,197,350 | 4/1980 | Kleber et al. ............ 428/392 |
| 4,264,516 | 4/1981 | Hiestand ............... 260/404.5 |

FOREIGN PATENT DOCUMENTS 0021546 1/1981 European Pat. Off. .
0029172 5/1981 European Pat. Off. .

*Primary Examiner*—Charles F. Warren
*Assistant Examiner*—Mrs. Y. Harris-Smith
*Attorney, Agent, or Firm*—Sprung, Horn, Kramer & Woods

[57] ABSTRACT

Ammonium compounds of the formula $$\left[ \begin{array}{c} R' \\ | \\ R-COO-CH-CH \\ \\ R_1-COO-CH-CH_2 \\ | \\ R' \end{array} \underset{N}{\overset{\oplus}{\diagup}} \begin{array}{c} R_2 \\ \\ R_3 \end{array} \right] A^{\ominus} \quad (I)$$

in which
R and $R_1$ designate $C_1$–$C_{21}$-alkyl or $C_2$–$C_{21}$-alkenyl,
R' designates hydrogen or $C_1$–$C_4$-alkyl,
$R_2$ designates $C_1$–$C_4$-alkyl or hydroxy-$C_1$–$C_4$-alkyl,
$R_3$ designates hydrogen or $C_1$–$C_4$-alkyl and
$A^{\ominus}$ represents an anion of the formula $$R_4-\overset{O}{\underset{\diagdown}{\overset{||}{P}}}\overset{OR_5}{\underset{O^{\ominus}}{\diagup}}, \quad (II)$$

in which
$R_4$ designates hydrogen, $C_1$–$C_4$-alkyl or $C_1$–$C_4$-alkoxy and
$R_5$ designates $C_1$–$C_4$-alkyl or $C_1$–$C_4$-hydroxyalkyl, a process for their preparation and their use as softeners for fiber materials.

7 Claims, No Drawings

AMMONIUM COMPOUNDS

The invention relates to new ammonium compounds of the formula

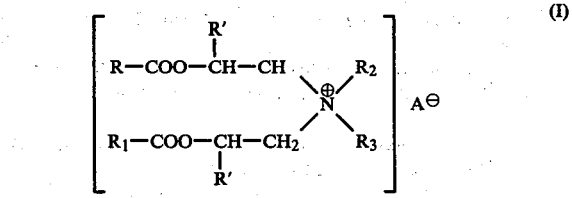

in which
R and $R_1$ designate $C_1$–$C_{21}$-alkyl or $C_2$–$C_{21}$-alkenyl,
R' designates hydrogen or $C_1$–$C_4$-alkyl,
$R_2$ designates $C_1$–$C_4$-alkyl or hydroxy-$C_1$–$C_4$-alkyl,
$R_3$ designates hydrogen or $C_1$–$C_4$-alkyl and
$A^\ominus$ represents an anion of the formula

in which
$R_4$ designates hydrogen, $C_1$–$C_4$-alkyl or $C_1$–$C_4$-alkoxy and
$R_5$ designates $C_1$–$C_4$-alkyl or $C_1$–$C_4$-hydroxyalkyl,
a process for their preparation and their use as softeners for fibre materials.

The following meanings of individual substituents are preferable:
R or $R_1$ $C_{11}$–$C_{21}$-alkyl or $C_{11}$–$C_{21}$-alkenyl; R' hydrogen or methyl; $R_3$ methyl or ethyl; $R_4$ hydrogen, methyl, ethyl, methoxy or ethoxy; and $R_5$ methyl or ethyl.

Those compounds of the formula I are particularly preferable in which $R_2$ designates methyl and $R_3$ designates hydrogen, methyl or ethyl.

Preferable anions $A^\ominus$ are:

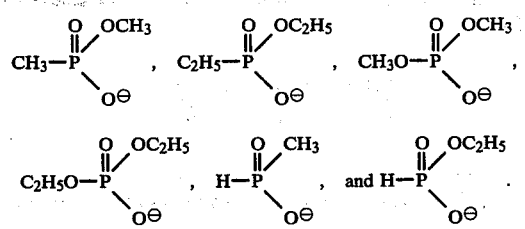

Ammonium compounds of the formula I are prepared by reacting esters of the formula

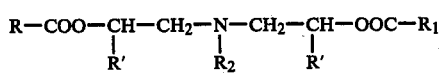

in which
R, R', $R_1$ and $R_2$ have the meanings indicated in the formula I
at temperatures of about 50° to about 200° C., preferably at 100°–150° C., with compounds of the formula

in which
$R_3$, $R_4$ and $R_5$ have the meanings indicated in the formulae (I) and (II).

The new compounds are obtained here as solid or pasty products which are readily soluble or dispersible in water.

Preferable compounds are obtained by reacting esters of the formula

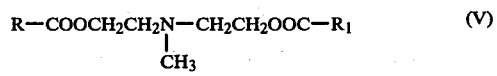

with trimethyl phosphate, triethyl phosphate, dimethyl methanephosphonate or diethyl ethanephosphonate, but in particular with dimethyl phosphite or diethyl phosphite.

Esters of the formulae III or V can be prepared in a manner which is in itself known, for example by reaction of 2 mols of a corresponding carboxylic acid or of its low alkyl ester with 1 mol of a compound of the formula

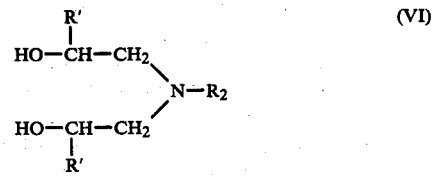

in which
R' and $R_2$ have the meanings indicated in the formula I
at temperatures of 100° to 180° C., water formed during the reaction or the lower alcohol being continuously removed from the reaction mixture. For the case that $R \neq R_1$ the amine can first be reacted with one mol of a carboxylic acid and the product then reacted with one mol of another carboxylic acid.

Possible examples of carboxylic acids are not only pure acids, such as lauric acid, myristic acid, palmitic acid, stearic acid, arachidic acid, behenic acid, oleic acid or linoleic acid, but also, if appropriate, acid mixtures, such as possibly hydrogenated fatty acid mixtures on which natural fats are based or fractions of such fatty acid mixtures.

The new ammonium compounds are suitable for use as softeners for fiber materials, such as textile fiber materials made of synthetic fibers for example of polyester, polyacrylonitrile or polyamide fibers, and, in particular, of cotton or regenerated cellulose fibers. They are also suitable for use as softening agents for paper.

The new compounds are applied to fibre materials in a manner which is customary for softeners, for example by the exhaust method from a long liquor. For this purpose, 0.1 g to 10 g of the new compounds per liter of water are dissolved or dispersed. On application by the pad method, amounts of 5–25 g per liter of liquor are advantageously used.

In the examples which follow, parts are parts by weight.

EXAMPLE 1

241 parts of hydrogenated coconut fatty acid and 22 parts of stearic acid are dissolved in 60 parts of toluene, 75 parts of N-methyl-N,N-diethanolamine are added, and the mixture is heated to 130°–140° C., water formed being distilled off azeotropically.

After toluene has been distilled off, 65 parts of dimethyl phosphite are added to the resulting ester, and the mixture is heated for 4–5 hours at 140° C. After cooling down, the mixture is obtained as a viscous liquid which gives a slightly turbid solution in water. The surface tension of an 0.5% strength aqueous solution at 20° C. is 31.4 mN.m$^{-1}$.

EXAMPLE 2

35 parts of dimethyl methanephosphonate are added to 165 parts of an ester prepared analogously to Example 1 from 1 mol of stearic acid and 1 mol of lauric acid with 1 mol of N-methyl-N,N-diethanolamine, and the mixture is stirred for 6 hours at 140° C. The result is a water-soluble product which, at room temperature, solidifies to give a pasty material. The surface tension of an 0.5% strength aqueous solution at 20° C. is 35.9 mN.m$^{-1}$.

EXAMPLE 3

0.5% of the product of Example 1 (relative to the weight of the goods) is dissolved 1:10 in water, and the solution is added to an aqueous liquor, the amount of which, in proportion to the weight of the goods, is 1:20.

The textile material used is cotton terry towelling having a weight per square meter of 100 g/m$^2$. The treatment temperature is 40° C., and the treatment time is 30 minutes. The material is then squeezed, in a pad mangle, down to a liquor pick-up of 100% and dried 2–3 minutes at 120° C. The result is a pleasant, soft handle.

EXAMPLE 4

15 g of the ammonium compound prepared according to Example 2 are dissolved 1:10 in water at 40° C. The solution is made up to 1 liter with water. Cotton terry towelling having a square meter weight of 180 g/m$^2$ is dipped into the liquor and squeezed off, in a pad mangle, down to a liquor pick-up of 90%. The material is then dried for 2–3 minutes at 120° C. The result is terry towelling fabric having a pleasant, soft handle.

We claim:

1. Ammonium compounds of the formula

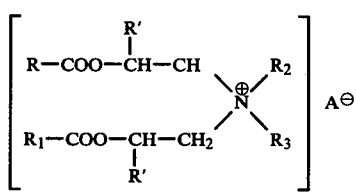

in which

R and $R_1$ designate $C_1$–$C_{21}$-alkyl or $C_2$–$C_{21}$-alkenyl,
R' designates hydrogen or $C_1$–$C_4$-alkyl,
$R_2$ designates $C_1$–$C_4$-alkyl or hydroxy-$C_1$–$C_4$-alkyl,
$R_3$ designates hydrogen or $C_1$–$C_4$-alkyl and
$A^{\ominus}$ represents an anion of the formula

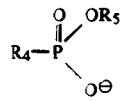

in which $R_4$ designates hydrogen, $C_1$–$C_4$-alkyl or $C_1$–$C_4$-alkoxy and
$R_5$ designates $C_1$–$C_4$-alkyl or $C_1$–$C_4$-hydroxyalkyl.

2. Compounds according to claim 1, in which, in the formula I,

R and $R_1$ designate $C_{11}$–$C_{21}$-alkyl or $C_{11}$–$C_{21}$-alkenyl,
R' designates hydrogen or methyl,
$R_2$ designates $C_1$–$C_4$-alkyl or hydroxy-$C_1$–$C_4$-alkyl,
$R_3$ designates methyl or ethyl,
$R_4$ designates hydrogen, methyl, ethyl, methoxy, or ethoxy and
$R_5$ designates methyl or ethyl.

3. Compounds according to claims 1 and 2, in which $R_2$ designates methyl and $R_3$ designates hydrogen, methyl or ethyl.

4. Compounds according to claims 1 to 3, characterised in that $A^{\ominus}$ represents a

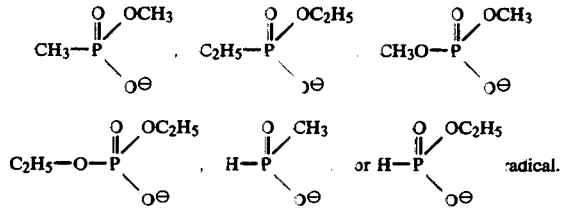

radical.

5. Ammonium compounds which can be obtained by reacting compounds of the formula

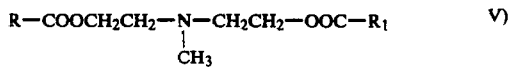

with trimethyl phosphate, triethyl phosphate, dimethyl methanephosphonate or diethyl ethanephosphonate, but, in particular, with dimethyl phosphite or diethyl phosphite.

6. Process for preparing ammonium compounds according to claim 1, characterized in that esters of the formula

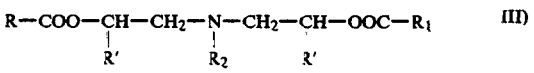

in which

R, R', $R_1$ and $R_2$ have the meanings indicated in claim 1 at temperatures of about 50° to about 200° C. with compounds of the formula

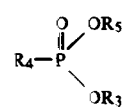

in which $R_3$, $R_4$ and $R_5$ have the meanings indicated in claim 1.

7. Use of compounds according to claims 1 to 5, as softeners for fibre materials.

* * * * *

UNITED STATES PATENT AND TRADEMARK OFFICE
CERTIFICATE OF CORRECTION

PATENT NO. : 4,456,554
DATED : June 26, 1984
INVENTOR(S) : Klaus Walz et al.

It is certified that error appears in the above-identified patent and that said Letters Patent is hereby corrected as shown below:

Col. 1, line 9 and
   Col. 3, line 56

Insert "$_2$" after "CH" as follows:

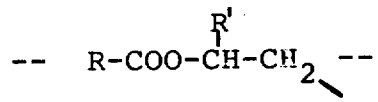

$$-- \text{R-COO-}\overset{R'}{\underset{|}{C}}\text{H-CH}_2 --$$

Signed and Sealed this

*Twenty-seventh* Day of *November 1984*

[SEAL]

*Attest:*

*Attesting Officer*

GERALD J. MOSSINGHOFF
*Commissioner of Patents and Trademarks*